United States Patent [19]

Beriger

[11] 4,123,551
[45] Oct. 31, 1978

[54] 2,2-DISUBSTITUTED-PHENYLCARBAMOYL-6-HYDROXY-M-DIOXIN-4-ONE DERIVATIVES HAVING INSECTICIDAL PROPERTIES

[75] Inventor: Ernst Beriger, Allschwil, Switzerland

[73] Assignee: Ciba-Geigy Corporation, Ardsley, N.Y.

[21] Appl. No.: 758,260

[22] Filed: Jan. 10, 1977

[30] Foreign Application Priority Data

Jan. 14, 1976 [CH] Switzerland ............................ 396/76
Jul. 28, 1976 [CH] Switzerland .......................... 9639/76
Dec. 14, 1976 [CH] Switzerland ........................ 15700/76

[51] Int. Cl.$^2$ ..................... A01N 9/28; C07D 319/06; C07D 319/08
[52] U.S. Cl. .................................... 424/279; 260/340.2
[58] Field of Search ...................... 260/340.2; 424/279

[56] References Cited

U.S. PATENT DOCUMENTS

| | | | |
|---|---|---|---|
| 2,432,118 | 12/1947 | Muller et al. | 424/278 |
| 2,939,872 | 6/1960 | Hudson | 260/348 |
| 3,931,171 | 1/1976 | Jager et al. | 260/340.2 |
| 4,008,067 | 2/1977 | Hirono et al. | 260/340.2 |
| 4,073,932 | 2/1978 | Beriger | 424/279 |

OTHER PUBLICATIONS

U. Herzog et al., Eur. J. Med. Chem.-Chim. Ther. (1975) 10(3), pp. 323–325, as abstracted in Chemical Abstracts, vol. 84 (1976) 59338d.

*Primary Examiner*—Norma S. Milestone
*Attorney, Agent, or Firm*—Harry Falber

[57] ABSTRACT

Compounds of the formula I wherein
$R_1$ represents a phenyl group substituted by one or two members selected from the group consisting of halogen, alkyl having at most 3 carbon atoms, trifluoromethyl, nitro and cyano; and either
(i) $R_2$ represents an alkyl group having at most 5 carbon atoms and
$R_3$ represents a methyl group or
(ii) $R_2$ and $R_3$ together represent a tetramethylene or pentamethylene group;

with the proviso that, when $R_2$ and $R_3$ both represent methyl groups or when $R_2$ and $R_3$ together represent a tetramethylene or pentamethylene group, $R_1$ may not represent a 3-chlorophenyl, 4-chlorophenyl, 3,4-dichlorophenyl or 4-fluorophenyl group, possess valuable insecticidal properties.

5 Claims, No Drawings

2,2-DISUBSTITUTED-PHENYLCARBAMOYL-6-HYDROXY-M-DIOXIN-4-ONE DERIVATIVES HAVING INSECTICIDAL PROPERTIES

The present invention provides novel 2,2-disubstituted-5-phenylcarbamoyl-6-hydroxy-m-dioxin-4-one derivatives having insecticidal properties, a process for their manufacture, pesticidal compositions which contain these derivatives as active component, and a method of combating pests which comprises the use of the novel compounds.

The novel 2,2-disubstituted-5-phenylcarbamoyl-6-hydroxy-m-dioxin-4-one derivatives have the formula I

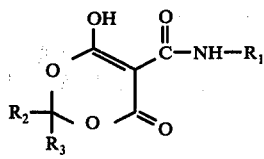

(I)

wherein
$R_1$ represents a phenyl group substituted by one or two members selected from the group consisting of halogen, alkyl having at most 3 carbon atoms, trifluoromethyl, nitro and cyano; and either
(i) $R_2$ represents an alkyl group having at most 5 carbon atoms and $R_3$ represents a methyl group or
(ii) $R_2$ and $R_3$ together represent a tetramethylene or pentamethylene group;
with the proviso that, when $R_2$ and $R_3$ both represent methyl groups or when $R_2$ and $R_3$ together represent a tetramethylene or pentamethylene group, $R_1$ may not represent a 3-chlorophenyl, 4-chlorophenyl, 3,4-dichlorophenyl or 4-fluorophenyl group.

Alkyl groups can be branched or straight-chain. Suitable examples of such substituents are the methyl, ethyl, n-propyl, iso-propyl, n-butyl, iso-butyl, sec.-butyl and tert.-butyl group, and the n-pentyl group and the isomers thereof. The term "halogen" is to be understood as meaning fluorine, chlorine, bromine and iodine, chiefly chlorine and bromine.

Particularly important compounds on account of their action against insects are those of the formula I wherein either (i) $R_2$ represents a methyl or ethyl group and $R_3$ represents a methyl group or (ii) $R_2$ and $R_3$ together represent a tetramethylene or pentamethylene group, and the most preferred compounds are those wherein $R_1$ represents a phenyl group which is substituted by one or two members selected from the group consisting of halogen, methyl and/or trifluoromethyl.

The compounds of the formula I, which are themselves novel, are obtained by methods known per se, for example by
(a) reacting an ester of the formula II

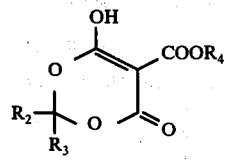

(II)

with an aniline of the formula III

, $R_1$—$NH_2$ (III);

(b) reacting a compound of the formula IV

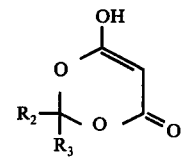

(IV)

with an isocyanate of the formula V $R_1$—NCO (V); or (c) treating a compound of the above formula IV with an azide of the formula VI $R_1$—CO—$N_3$ (VI)

In the above formulae II to VI, the symbols $R_1$ to $R_3$ are as defined in formula I and $R_4$ represents a $C_1$-$C_4$-alkyl group.

The starting materials of the formulae II and IV are partly known [see e.g. "Chem. Ber." 94, 929 (1961) and "Tetrahedron Letters" 7, 1 (1959)], and all these compounds can be obtained by methods analogous to the known ones.

Processes (a) and (c) are preferably carried out at a reaction temperature between 100° and 200° C. and process (b) at a reaction temperature between 0° and 200° C. The reactions can be carried out at normal or elevated pressure, optionally in a solvent or diluent which is inert to the reactants and optionally in the presence of a base.

Examples of suitable solvents or diluents for these reactions are: ethers and ethereal compounds, such as dipropyl ether, dioxane, dimethoxyethane and tetrahydrofurane; amides, such as dialkylated carboxamides; aliphatic, aromatic and halogenated hydrocarbons, in particular toluene, xylenes, and chlorobenzene; nitriles, such as acetonitrile; dimethyl sulphoxide; and ketones, such as acetone and methyl ethyl ketone.

Suitable bases are for example tertiary amines, such as triethylamine, dimethyl aniline, pyridine, picolines and lutidines, as well as the hydroxides, oxides, carbonates and bicarbonates of alkali metals and alkaline earth metals, and the alkali metal alcoholates, for example potassium tert. butylate and sodium methylate.

The compounds of the formula I, wherein $R_2$ represents a $C_2$-$C_5$-alkyl group, possess different optically active forms. If, therefore, individual isomers are not used as starting materials in the reaction, then racemic mixtures are necessarily obtained.

The different mixtures of isomers obtained can be separated into the individual isomeric forms for example by recrystallisation or with the aid of chromatographic separating methods, for example by gas chromatography or by adsorption on a separating material with selective adsorption activity (e.g. silica gel and alumina) and subsequent elution of the separated isomers with a suitable solvent. It will be understood that the compounds of the present invention comprise both the indivual optically active enantiomers and the mixtures thereof.

According to the present invention, it has now surprisingly been found that the compounds of the formula I possess a good action against insects that are harmful to plants and animals.

In particular, the compounds of the formula I have an effective action against insects of the order *Colleoptera*, chiefly of the families *Chrysomelidae* and *Curculionidae* (for example *Leptinotarsa decemlineata* and *Anthanomus grandis*) and accordingly are suitable for controlling insects in cotton plantations and crops of vegetables. In addition, individual compounds of the formula I act effectively against ectoparasitic insects (for example *Lucilia sericata*) and insects which are harmful in the sectors of hygiene and storage protection (for example *Musca domestica*), and can be used primarily for treating stored goods and for external application to productive livestock or for treating their environment. The insecticidal action can be substantially broadened and adapted to prevailing circumstances by the addition of other insecticides and/or acaricides.

Examples of suitable additives are: organic phosphorus compounds, nitrophenols and derivatives thereof, formamidines, ureas, pyrethroids, carbamates, and chlorinated hydrocarbons.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dust, emulsion concentrates, granules, dispersions, sprays, solutions or suspensions, such as are commonly employed in application technology.

The compositions according to the invention are obtained in known manner by homogeneously mixing and/or grinding active substances of the formula I with the suitable carriers, with or without the addition of dispersants or solvents which are inert to the active substances.

The compounds of the formula I may be formulated as follows:

Solid formulations: Dusts, tracking agents, granules (coated granules, impregnated granules and homogeneous granules).

Liquid formulations: (a) active substance concentrates which are dispersible in water: wettable powders, pastes, emulsions; (b) solutions.

The content of active substance in the above described compositions is between 0,1% and 95%, in which connection it must be mentioned that higher concentrations can also be used if the compositions are applied from an aircraft or other appropriate application devices.

The compounds of the formula I can, for example, for formulated as follows:

Dusts

The following substances are used to obtain (a) a 5% and (b) a 2% dust:

(a)

5 parts of active substance,
95 parts of talcum;

(b)

2 parts of active substance,
1 part of highly disperse silicic acid,
97 parts of talcum.

The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance mixed with epichlorohydrin and the mixture is dissolved in 6 parts of acetone. The polyethylene glycol and cetyl polyglycol ether are then added. The resultant solution is sprayed on kaolin, and the acetone is subsequently evaporated in vacuo.

Wettable powder

The following constituents are used for the preparation of (a) a 40%, (b) and (c) a 25%, and (d) a 10% wettable powder:

(a)

40 parts of active substance,
5 parts of sodium ligninsulphonate,
1 part of sodium dibutylnaphthalenesulphonate.

(b)

54 parts of silicic acid,
25 parts of active substance,
4.5 parts of calcium ligninsulphonate,
1.9 parts of Champagne chalk-hydroxyethyl cellulose mixture (1:1),
1.5 parts of sodium dibutylnaphthalenesulphonate,
19.5 parts of silicic acid,
19.5 parts of Champagne chalk,
28.1 parts of kaolin.

(c)

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin.

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in appropriate mills and rollers to yield wettable powders which can be diluted with water to give suspensions of the desired concentration.

Emulsifiable concentrate

The following substances are used to produce a 10% emulsifiable concentrate:
10 parts of active substance,
3.4 parts of epoxidised vegetable oil,
3.4 parts of a combination emulsifier consisting of fatty alcohol polyglycol ether and alkyl aryl sulphonate calcium salt, 40 parts of dimethyl formamide,
43.2 parts of xylene.

By diluting such a concentrate with water it is possible to manufacture emulsions of the desired concentration.

Spray

The following constituents are used to prepare (a) a 5% and (b) a 95% spray:

(a)

5 parts of active substance,
1 part of epichlorohydrin,
94 parts of benzene (boiling limits 160° C.-190° C.

(b)

95 parts of active substance,
5 parts of epichlorohydrin.

The following Examples illustrate the invention in more detail.

EXAMPLE 1

Preparation of 2,2-dimethyl-5-(4-trifluoromethylphenylcarbamoyl)-6-hydroxy-m-dioxin-4-one To a solution of 14.4 g of isopropylidene malonate in 150 ml of dimethyl sulphoxide were added dropwise, at room temperature, 10.1 g of triethylamine and thereafter, at 20° to 30° C., 18.7 g of 4-trifluoromethylphenylisocyanate. The mixture was reacted for 12 to 15 hours at room temperature and the resultant solution was poured into a solution of 15 ml of concentrated hydrochloric acid in 350 ml of water. The precipitate which formed was collected with suction. Recrystallisation from 130 ml of acetone yielded the product of the formula

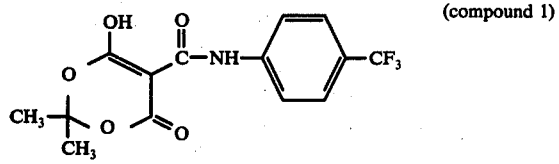

(compound 1)

with a melting point of 206°–208° C.

The following compounds of the formula Ia were obtained in analogous manner:

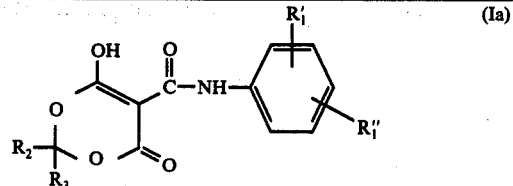

(Ia)

| Compound | R'₁ | R''₁ | R₂ | R₃ | Physical data |
|---|---|---|---|---|---|
| 2 | H | 4-Br | CH₃ | CH₃ | m.p. 203–206° C |
| 3 | H | 4-J | CH₃ | CH₃ | m.p. 217–220° C |
| 4 | H | 4-(i)C₃H₇ | CH₃ | CH₃ | m.p. 82–86° C |
| 5 | 3-CF₃ | H | CH₃ | CH₃ | m.p. 110–112° C |
| 6 | H | 4-NO₂ | CH₃ | CH₃ | m.p. 217–221° C |
| 7 | 2-Cl | 4-Cl | CH₃ | CH₃ | m.p. 230–234° C |
| 8 | 3-CF₃ | 5-CF₃ | CH₃ | CH₃ | m.p. 92–95° C |
| 9 | 3-Cl | 4-CF₃ | CH₃ | CH₃ | m.p. 210–213° C |
| 10 | H | 4-Cl | C₂H₅ | CH₃ | m.p. 100–102° C |
| 11 | 2-Cl | 4-Cl | C₂H₅ | CH₃ | m.p. 121° C |
| 12 | 3-Cl | 4-Cl | C₂H₅ | CH₃ | m.p. 130–131° C |
| 13 | H | 4-Br | —(CH₂)₄— | | m.p. 151° C |
| 14 | 2-Cl | 4-Cl | —(CH₂)₄— | | m.p. 133° C |
| 15 | H | 4-Br | —(CH₂)₅— | | m.p. 157–158° C |
| 16 | 2-Cl | 4-Cl | —(CH₂)₅— | | m.p. 135–138° C |
| 17 | 2-CH₃ | 4-Cl | CH₃ | CH₃ | m.p. 114–116° C |
| 18 | 2-CN | 4-Cl | CH₃ | CH₃ | m.p. 160° C |
| 19 | H | 4-Cl | iso-C₄H₉ | CH₃ | m.p. 91–92° C |
| 20 | H | 4-Cl | n-C₅H₁₁ | CH₃ | m.p. 99–102° C |
| 21 | H | 4-Cl | iso-C₃H₇ | CH₃ | m.p. 122° C |

EXAMPLE 2

Insecticidal stomach poison action (Leptinotarsa decemlineata)

Potato plants were sprayed with a 0.05% aqueous emulsion of the compound to the tested (obtained from a 10% emulsifiable concentrate).

After the spray coating had dried, the plants were populated with Leptinotarsa decemlineata larvae in the L₃-stage. Two plants were used per test and evaluation of the mortality achieved was made after 2, 4, 8, 24 and 48 hours respectively after the start of the test. The test was carried out at 24° C. and 60% relative humidity.

In the above test, compounds 1 to 3, 5, and 9 to 17 of Example 1 exhibited a good insecticidal stomach poison action (100% kill) on larvae of the species Leptinotarsa decemlineata.

EXAMPLE 3

Inhibition of damage caused by eating (Leptinotarsa decemlineata)

Two potato plants (15 cm in height) were sprayed with 25 ml of an acetone/water mixture (1:1) containing 0.01% of test substance.

After the spray coating had dried, each of the potato plants was populated with 10 larvae of the species Leptinotarsa decemlineata (L₃-stage). A plastic cylinder was then slipped over each plant to prevent the larvae from migrating. A copper gauze top was used to seal the cyclinder. The damage caused by eating was determined 2 days later.

In the above test, compounds of Example 1 effectively inhibited damage from eating. Compounds 1 to 3, 5, and 13 to 16 are to be singled out for their especially good action (only traces of damage were observed).

EXAMPLE 4

Insecticidal stomach poison/contact action (Anthanomus grandis)

Cotton plants in pots were sprayed with a spray broth containing 500 ppm of test substance (obtained from a 25% wettable powder) and allowed to dry. Each of the plants was then populated with 5 one-day-old insects of the species Anthanomus grandis and the plants were kept in greenhouse compartments at 24° C. and 60% relative himidity.

The number of dead and moribund insects was determined at intervals of 2, 4, 25 and 48 hours respectively after the start of the test. Two plants were used per test substance.

In the above test, the compounds of Example 1 exhibited a good action against insects of the species Anthanomus grandis.

EXAMPLE 5

Action against Musca domestica 50 g of freshly prepared CSMA nutrient substrate for maggots were charged into beakers. A specific amount of a 1% acetonic solution of the respective active substance was pipetted onto the nutrient substrate present in the beakers. The substrate was then thoroughly mixed and the acetone subsequently allowed to evaporate over a period of at least 20 hours.

Then 25 one-day-old maggots of Musca domestica were put into each of the beakers containing the treated nutrient substrate for testing with each active substance at one of its given concentrations. After the maggots had pupated, the pupae were separated from the substrate by flushing them out with water and then deposited in containers closed with a perforated top.

Each batch of flushed out pupae was counted to determine the toxic effect of the active substance on the maggot development. The number of flies which had hatched out of the pupae was then counted after 10 days and any influence on the metamorphosis thereby determined.

The compounds of the formula I acted well in this test against insects of the species Musca domestica. Compounds 1, 2, 3, 7 and 9 are to be singled out for their particularly good action (100% kill at 0.5 ml).

EXAMPLE 6

Action against Lucilia sericata

An aqueous solution containing 0.1% of test substance (2 ml) was added to 2 ml of a culture medium. Approx. 30 freshly hatched-out larvae of Lucilia sericata were then added to the culture medium and the insecticidal action was determined after 96 hours by evaluating the mortality rate.

In this test, the compounds of Example 1, especially compounds 1 to 3,5,7 to 12,14 and 17, acted well against larvae of Lucilia sericata.

What is claimed is:

1. A method of controlling insects in crop plants and on productive livestock which method comprises applying to said plants and livestock or their environment an insecticidally effective amount of a compound of the formula

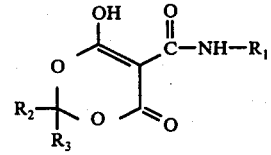

wherein $R_1$ is phenyl mono- or di- substituted by halogen, methyl or trifluoromethyl; and either $R_2$ is methyl or ethyl, and $R_3$ is methyl, or $R_2$ and $R_3$ together are tetramethylene or pentamethylene, with the proviso that when $R_2$ and $R_3$ both represent methyl groups or when $R_2$ and $R_3$ together represent a tetramethylene or pentamethylene group, $R_1$ may not represent 3-chlorophenyl, 4-chlorophenyl, 3,4-dichlorophenyl or 4-fluorophenyl.

2. The method of claim 1, wherein said compound is 2,2-dimethyl-5-(4-trifluoromethylphenyl-carbamoyl)-6-hydroxy-m-dioxin-4-one.

3. The method of claim 1, wherein said compound is 2,2-dimethyl-5-(4-bromophenylcarbamoyl)-6-hydroxy-m-dioxin-4-one.

4. The method of claim 1, wherein said compound is 2,2-dimethyl-5-(3-chloro-4-trifluoromethyl-phenylcarbamoyl)-6-hydroxy-m-dioxin-4-one.

5. The method of claim 1, wherein said insect is an ectoparasitic insect of the class *Lucilia sericata*.